(12) United States Patent
Van Benthem et al.

(10) Patent No.: US 7,354,987 B2
(45) Date of Patent: Apr. 8, 2008

(54) NITROGEN-CONTAINING COMPOUND, THE PREPARATION THEREOF AND APPLICATION IN AMINO-ALDEHYDE RESINS

(75) Inventors: Rudolfus Antonius Theodorus Maria Van Benthem, Limbricht (NL); Renier Henricus Maria Kierkels, Beegden (NL); Jacobus Adriaan Antonius Vermeulen, Geleen (NL)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 11/707,952

(22) Filed: Feb. 20, 2007

(65) Prior Publication Data

US 2007/0149753 A1    Jun. 28, 2007

Related U.S. Application Data

(62) Division of application No. 10/516,113, filed as application No. PCT/NL03/00399 on May 28, 2003, now Pat. No. 7,199,209.

(30) Foreign Application Priority Data

May 30, 2002    (NL) .................... 1020720

(51) Int. Cl.
    *C08G 12/30*    (2006.01)
    *C08G 12/32*    (2006.01)
(52) U.S. Cl. .............. 528/254; 528/230; 528/243; 528/245
(58) Field of Classification Search ......... 528/254, 528/230, 245, 243
    See application file for complete search history.

(56) References Cited

U.S. PATENT DOCUMENTS 4,770,668 A    9/1988   Skoultchi et al.

5,681,917 A    10/1997  Breyer

FOREIGN PATENT DOCUMENTS

JP    EP0976738    2/2000

*Primary Examiner*—Duc Truong
(74) *Attorney, Agent, or Firm*—Nixon & Vanderhye P.C.

(57) ABSTRACT

The invention relates to a compound of formula I:

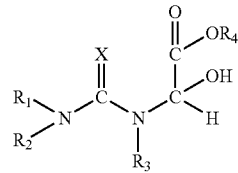

(I)

where:
X is equal to $NR^5$;
$R^4$ is equal to a C1-C12 alkyl group, aryl group, aralkyl group or cycloalkyl group.
$R^1$, $R^2$, $R^3$, $R^5$ are equal to an H, alkyl, cycloalkyl, aryl of heterocyclic group;
where $R^1$, $R^2$, and $R^5$ or $R^1$, $R^2$, and $R^3$ may together form a heterocyclic group. The invention also relates to a method for the preparation of this compound by reaction of an amino compound with an alkanol hemiacetal. The invention also relates to amino-aldehyde resins containing this compound and the application of these resins in adhesive compositions, laminates, shaped articles and transparent coatings.

15 Claims, No Drawings

NITROGEN-CONTAINING COMPOUND, THE PREPARATION THEREOF AND APPLICATION IN AMINO-ALDEHYDE RESINS

CROSS-REFERENCE TO RELATED APPLICATION

This application is a divisional of U.S. application Ser. No. 10/516,113 filed on Nov. 30, 2004, now U.S. Pat. No. 7,199,209 which is the National Phase of International Application PCT/NL03/0399 filed May 28, 2003 which designed the U.S., and was published in English, the entire content of which is expressly incorporated hereinto by reference.

The invention relates to a nitrogen-containing compound as well as the preparation thereof. The invention also relates to amino-aldehyde resins containing a nitrogen-containing compound, and their application in adhesive compositions, laminates, shaped articles and coatings.

Amino-aldehyde resins, such as for example melamine-formaldehyde (MF), urea-formaldehyde (UF) and melamine-urea formaldehyde (MUF) are commonly known. Such resins are obtained by the reaction of one or more amino compounds with formaldehyde as described in for example U.S. Pat. No. 5,681,917. U.S. 5,681,917 describes a stable melamine-urea-formaldehyde resin with low formaldehyde emission. The resin is particularly suitable as a binding agent for the preparation of a composite material.

An important drawback of the resin from U.S. Pat. No. 5,681,917 is that a slight formaldehyde emission is still observed. In the production of the resin and in the production of the composite material, among other things, vapours are released that may be irritating. Residues of the original raw materials always remain behind, also after polymerization. In cured condition, formaldehyde slowly diffuses from the product. This formaldehyde emission is not desirable, definitely not in a confined area. In such areas formaldehyde is inhaled and contacts the eyes, mouth and other parts of the body. Formaldehyde gas causes irritation of the eyes and respiratory tract.

The object of the invention is to provide a compound for application in resins, adhesives, laminates, shaped articles and coatings that does not have the aforementioned drawback.

This is achieved by the compound of the following formula:

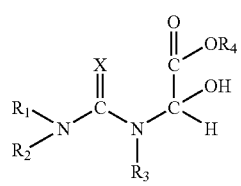

where:
X is equal to $NR_5$;
$R_4$ is equal to a $C_1$-$C_{12}$ alkyl group, aryl group, aralkyl group or cycloalkyl group.
$R_1$, $R_2$, $R_3$, $R_5$ are an H, alkyl, cycloalkyl, aryl of heterocyclic group;
where $R_1$, $R_2$, and $R_5$ or $R_1$, $R_2$, and $R_3$ may together form a heterocyclic group.

Preferably $R_4$ is a $C_1$-$C_{12}$ alkyl group. Examples hereof are methyl, ethyl, propyl, butyl, pentyl, hexyl, heptyl etc. $R_4$ is in particular a methyl group or an ethyl group.

The advantage of the compound of the invention is that when amino-aldehyde resins are prepared with this compound there is, compared to the amino-formaldehyde resins which are the current standard in practice, no, or only a reduced need to use formaldehyde in the resin preparation so that formaldehyde emission diminishes or is even completely absent and the resin is suitable for the same applications as described in U.S. Pat. No. 5,681,917. Thus, resins prepared with the compound according to the present invention are in particular suitable for use in many applications, such as adhesives, laminates, shaped articles and coatings.

The invention also relates to a process for the preparation of the compound according to formula (I) by reacting an amino compound and an alkanol hemiacetal of the following general formula (II):

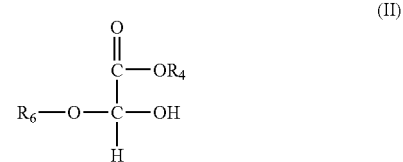

where $R_4$ and $R_6$ are a $C_1$-$C_{12}$ alkyl group, aryl group, aralkyl group or cycloalkyl group, in which process an alkanol is released.

Preferably $R_4$ and $R_6$ are $C_1$-$C_{12}$ alkyl groups. Examples hereof are methyl, ethyl, propyl, butyl, pentyl, hexyl, heptyl etc. $R_4$ and $R_6$ are in particular a methyl group or an ethyl group.

Examples of alkanol hemiacetals of formula II are:
methylglyoxylate methanol hemiacetal (GMHA®, DSM Fine Chemicals, Linz);
ethylglyoxylate ethanol hemiacetal (GEHA®, DSM Fine Chemicals, Linz);
ethylglyoxylate methanol hemiacetal; butylglyoxylate butanol hemiacetal;
butylglyoxylate methanol hemiacetal; butylglyoxylate ethanol hemiacetal;
isopropylglyoxylate isopropanol hemiacetal; propylglyoxylate propanol hemiacetal;
cyclohexylglyoxylate methanol hemiacetal and 2-ethylhexylglyoxylate methanol hemiacetal.

An amino compound is defined herein as a compound having at least one NH or $NH_2$ group, attached to an electron-withdrawing atom or to an atom that is connected to electron-withdrawing atom or group. Examples of electron-withdrawing atoms are oxygen, nitrogen and sulphur. Suitable amino compounds are for example triazines, guanidine and mixtures of these compounds. Aminoplasts such as melamine-formaldehyde, urea-formaldehyde and melamine-urea-formaldehyde may also be employed as amino compound. Preferably, triazines such as melamine, melam, melem, ammeline, ammelide and ureidomelamine are used. In particular melamine is used.

The process for the preparation of the compound according to formula (I) according to the invention will usually occur spontaneously once the amino compound and the alkanol hemiacetal according to formula (II) have been brought into contact with each other. The temperature in the present process can thus vary within wide limits, and preferably lies between 10° C. and 100° C. Most preferably the process is carried out at between 40° C. and 90° C. The pressure in the present process preferably is between 0.005 MPa and 1.0 MPa, preferably between 0.02 MPa and 1.0 MPa. The process is preferably carried out in a liquid dispersant such as for example water or a mixture of water and alkanol. Water is the preferred dispersant. Examples of alkanols are methanol, ethanol, propanol, butanol, pentanol etc. It is not always necessary to use such a dispersant, however, since many of the compounds according to formula (II) are a liquid at room temperature and can thus act as reactant and dispersant.

The invention further relates to the preparation of amino-aldehyde resins comprising the condensation product of a compound of formula (III).

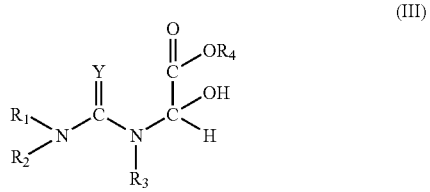

where:

Y is equal to O or $NR_5$;

$R_4$ is equal to a $C_1$-$C_{12}$ alkyl group, aryl group, aralkyl group or cycloalkyl group.

$R_1$, $R_2$, $R_3$, $R_5$ are an H, alkyl, cycloalkyl, aryl of heterocyclic group;

where $R_1$, $R_2$, and $R_5$ or $R_1$, $R_2$, and $R_3$ may together form a heterocyclic group.

The compound of formula (III) may be prepared in the same fashion as the preparation of the compound of formula (I). In the preparation of the compound of formula (III), suitable amino compounds include for example triazines, glyco-uril, urea, guanidine and mixtures of these compounds. Aminoplasts such as melamine-formaldehyde, urea-formaldehyde and melamine-urea-formaldehyde may also be employed as amino compound. Preferably, urea and triazines such as melamine, melam, melem, ammeline, ammelide and ureidomelamine are used. In particular, urea and/or melamine is used.

The amino-aldehyde resin according to the invention may be prepared by combining the compound according to formula (III) with a dispersant such as water, followed by stirring at elevated temperature, i.e. a temperature above room temperature, and optionally at reduced pressure, i.e. at a pressure below atmospheric pressure. It is possible according to the invention to add mixtures of different alkanol hemiacetals according to formula (II) or a mixture of formaldehyde and one or more of such alkanol hemiacetal(s). If formaldehyde is added, it is preferably done so in a molar amount of 60% or less compared to the molar amount of alkanol hemiacetal, more preferably 40% or less, most preferably 20% or even 10% or less. Furthermore, it is possible according to the process of the invention that, in addition to the compound according to formula (III), other amino compounds such as urea and/or melamine are added. A catalyst may be used in the condensation process. Both acids and bases may be used to this end. It is preferred not to use a catalyst. Suitable examples of acid catalysts are sulphuric acid, nitric acid, hydrochloric acid, phosphoric acid, boric acid, tetrafluoroboric acid, paratoluene sulphonic acid, formic acid, ammonium sulphate, ammonium chloride, ammonium nitrate. Suitable examples of basic catalysts are ammonia, trimethyl amine, triethyl amine, DABCO (diaza-bicyclo-octane), DBU (diaza-bicyclo-undecene), DMAP (4-dimethylaminopyridine), sodium hydroxide, potassium hydroxide.

The condensation usually takes place at a temperature of 60° C. to 100° C. with water and/or alkanol being split off. The condensation reaction optionally takes place simultaneously with the synthesis of the reaction products of formula (I). The optionally reduced pressure is advantageous in that it facilitates the removal of products of the various possible condensation reactions, mostly water and/or alkanol. Operation at reduced pressure and the removal of water and/or alkanol are not required for preparation of the resin. In general, operation at reduced pressure and removal of products of the various possible condensation reactions will lead to faster resin preparation. The resin is preferably prepared at a pressure of between 0.005 MPa and 1 MPa. More preferably, the resin is then prepared at a pressure of between 0.02 MPa and atmospheric pressure. The type of atmosphere under which the resin preparation takes place is generally unimportant and may be thus be air or optionally an inert gas, such as for instance nitrogen.

The molar ratio of the amino compound to aldehyde compound generally is between 1:0.1 and 1:3.0. The molar ratio preferably is between 1:0.5 and 1:2.

Additives may be added to the resin before the resin is used for processing in its final application. Examples of customary additives are mould release agents, antistatic agents, adhesion promoters, plasticizers, colour enhancing agents, flame retardants, fillers, flow promoters, colorants, diluents, polymerization initiators, UV-stabilizers and heat stabilizers. Examples of fillers are glass fibres, mica, carbon fibres, metal fibres, clay, aramide fibres and strong polyethylene fibres.

The resins may be used in laminates, shaped articles and transparent coatings. A catalyst may be added If necessary for the resin to cure in the laminate, the shaped article or the coating. Acids, bases and Lewis acids may be used as a catalyst. Suitable examples of acid catalysts are sulphuric acid, nitric acid, hydrochloric acid, phosphoric acid, boric acid, tetrafluoroboric acid, paratoluene sulphonic acid, formic acid, ammonium sulphate, ammonium chloride, ammonium nitrate. Suitable examples of basic catalysts are ammonia, trimethyl amine, triethyl amine, DABCO (diaza-bicyclo-octane), DBU (diaza-bicyclo-undecene), DMAP (4-dimethylaminopyridine), sodium hydroxide, potassium hydroxide. Suitable examples of Lewis acid catalysts are zinc acetate, zinc chloride, magnesium chloride, magnesium bromide, titaniumtetrachloride, titaniumtetrabutoxide, titaniumacetylacetonate, zirconiumtetrabutoxide, borotrifluoride (-diethylether), lithium chloride.

Amino-aldehyde resins according to the invention may be applied in laminates, for example in high-pressure laminates (HPL) and low-pressure laminates (LPL). To this end one or more sheet-shaped carrier materials impregnated with the resin are compressed to form a shaped final product. The laminate may optionally contain polymer layers. The surface of the final product may be fashioned as desired with the aid of techniques known to one skilled in the art. A high-gloss surface, for instance, may be obtained by using for example a glazing plate in the press, a glazing membrane or a glazed (polished) mould. Relief can be provided on and in the surface by applying for example an etched or engraved plate in the pressing operation or by using a membrane or press or mould having relief. Patterns may similarly be provided. It is also possible, for instance, to apply films between the pressing plate or membrane and the shaped article. These films, in turn, may be smooth, matt or have the desired pattern or relief. Direct lamination, too, is an application of the resins of the present invention.

Shaped articles based on amino-aldehyde resins of the invention may be obtained in various ways. The resin may be applied as, for example, a casting resin. This for instance involves pouring the resin into a mould and curing it, following which a shaped article of a desired design is obtained. The resin is also well suitable for use as impregnation resin. A carrier material may be passed through a bath containing resin of suitable viscosity, or the resin may be applied to the carrier material in a different way. Examples of suitable carrier materials are woven or non-woven materials based on fibres, yarns or strands of, for instance, cellulose, cellulose acetates, manmade silk, cotton, wool, glass, rock wool, thermoplastic polymers or mixtures of different materials.

Shaped articles made of or with amino-aldehyde resins of the invention generally possess a number of highly favourable properties such as surface hardness, flame retardance, easy colourability and high scratch resistance.

Examples of objects made of or with amino-aldehyde resins of the invention are laminate floors, skirting boards, desk tops with a cured laminate top layer, structural mouldings on the present amino-aldehyde resin and an inorganic filler, dinner trays, washing-up bowls, lampshades, (corrugated) sheets, doors, kitchen tops, furniture, wall panelling and tableware. Tableware based on the present amino-aldehyde resin is particularly suitable for use in microwave ovens.

The resin of the invention is also eminently suitable for use as a coating. The resin is easy to apply in a thin layer on surfaces as a solution or as a powder and then to pressure-cure. As a substrate for the coating many materials can be used, for instance glass and wood or wood-based materials such as, for instance, medium density fibreboard (MDF), high density fibreboard (HDF), chipboard and oriented-strand board (OSB), and plastics such as, for instance, polyethylene and polypropylene, and metals such as, for instance, aluminium, steel and iron and paper-based or cellulose-fibre-based materials such as LPL laminates, HPL laminates, Trespa Athlon®, Trespa Metaon® and Trespa Toplab® from Trespa B.V. and the like. The coatings obtained are very hard, have an excellent solvent resistance, and are clear, colourless and scratch resistant. The resin is also suitable for use as coating for textile fibres such as cotton and cellulose. The coating reduces shrink and crease of the fibres.

The resin may also be used for the preparation of an adhesive to be applied in board material by combining cellulose-containing materials with an adhesive in a press and producing board material therein at elevated temperature and pressure. Preferably the process is used in the production of multiplex, chipboard, MDF board (medium-density fibreboard), HDF board (high-density fibre board) or OSB board (oriented-strand board).

Normally the adhesive of the invention is prepared shortly before the board is produced, by optionally adding a catalyst to the resin. After addition of the catalyst to the resin, the adhesive is in general used for 10 seconds to 1 hour for the preparation of board material, preferably for 30 seconds to 30 minutes. The pressing conditions during the preparation of board material are dependent on the type of board material. For the production of multiplex, for example, a pressure of 1-2 MPa is usually applied, for chipboard a pressure of usually 1-5 MPa, preferably 2-4 MPa, and for MDF a pressure of usually 2-7 MPa, preferably 3-6 MPa. The temperature at which the board material is manufactured is generally 100-160° C. for multiplex, generally 180-230° C. for chipboard and OSB and generally 170-230° C. for MDF. In the case of multiplex the board is kept under said conditions for 5-10 minutes (holding time). For chipboard, MDF and OSB a holding time is applied which is expressed in seconds per mm board thickness. For OSB board the holding time is generally 4-12 sec/mm, preferably 6-10 sec/mm. For chip board the holding time usually is 4-12 sec/mm, preferably 5-10 sec/mm. MDF boards are manufactured with a holding time of generally 5-17 sec/mm, in particular 8-14 sec/mm.

During the adhesive preparation waxes are usually added to the adhesive composition to make the final board material more resistant to moisture absorption. The waxes usually are emulsion waxes or solid waxes and originate for example from the petroleum industry.

The invention is elucidated with reference to the following example.

EXAMPLE I

For the preparation of a melamine/methylglyoxylate laminating resin with a solids content of 75% 14.5 grams of melamine are dissolved, in about 20 minutes, in a warm (80° C.) solution of 21.1 grams of methylglyoxylate methanol hemiacetal in 15 ml of water. The clear solution is cooled to room temperature; the resin solution remains clear for some hours at room temperature. Filter paper (Machery-Nagel) is impregnated with the resin solution and dried in vacuo at 100° C. to a density of 110-150 grams of dry resin/100 grams of paper. The paper is pressed at 120° C. and at a pressure of 40 N/cm2 in 10 minutes. A virtually colourless and clear, transparent laminate is obtained. In a staining test ("Kiton-test", DIN-EN 438-2 (1991)) a minute amount of Rhodamine/HCl colorant remains in the laminate after 1 hour's exposure. When the paper is pressed in 10 minutes at 140° C. under a pressure of 40 N/cm2, a light yellow transparent, scratch-resistant laminate is obtained that absorbs no Rhodamine/HCl colorant at all in this test, indicative of a high-quality fully cured laminate. Since no formaldehyde was used in the preparation of the laminate, the formaldehyde emission is zero. The scratch resistance of the laminate was qualitatively evaluated by scratching it with the point of a scissor; this left no marks.

The invention claimed is:

1. Process for the preparation of a compound of formula I:

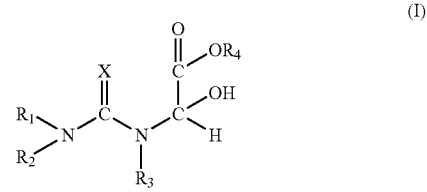

where:
X is equal to $NR_5$;
$R_4$ is equal to a $C_1$-$C_{12}$ alkyl group, aryl group, aralkyl group or cycloalkyl group;
$R_1$, $R_2$, $R_3$, $R_5$ are eaual to an H, alkyl, cycloalkyl, aryl or heterocyclic group;

where $R_1$, $R_2$, and $R_5$ or $R_1$, $R_2$, and $R_3$ may together form a heterocyclic group, the process comprising reacting an amino compound and an alkanol hemiacetal of the following general formula (II):

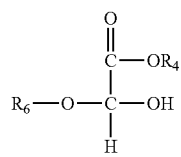
(II)

where $R_4$ and $R_6$ are a $C_1$-$C_{12}$ alkyl group, aryl group, aralkyl group or cycloalkyl group, in which process alkanol is released.

2. Process according to claim 1, wherein a triazine, or guanidine are used as an amino compound.

3. Process according to claim 1, wherein melamine, melam, melem, ammeline, ammelide or ureidomelamine is used as an amino compound.

4. Process according to claim 3, wherein melamine is used as an amino compound.

5. Process for the preparation of amino-aldehyde resins, wherein an amino compound is used of formula (III):

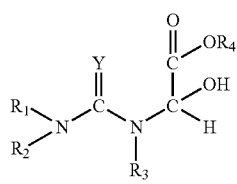
(III)

where:

Y is equal to O or $NR_5$;

$R_4$ is equal to a $C_1$-$C_{12}$ alkyl group, aryl group, aralkyl group or cycloalkyl group;

$R_1$, $R_2$, $R_3$, $R_5$ are an H, alkyl, cycloalkyl, aryl or heterocyclic group; and where $R_1$, $R_2$, and $R_5$ or $R_1$, $R_2$, and $R_3$ may together form a heterocyclic group.

6. Process according to claim 5, wherein urea and/or melamine are used in the preparation of the compound of formula (III).

7. Amino aldehyde resin prepared according to claim 5.

8. Amino aldehyde resins resin according to claim 5 wherein the molar ratio of amino compound to aldehyde compound is between 1:0.1 and 1:3:00.

9. Amino-aldehyde resin according to claim 8, wherein the molar ratio of amino compound to aldehyde compound is between 1:0.5 and 1:2.0.

10. Laminate produced with amino-aldehyde resin according to claim 7.

11. Shaped articles prepared from amino-aldehyde resin according to claim 7.

12. A coating which comprises an aldehyde resin according to claim 7.

13. Adhesive composition containing amino-aldehyde resin according to claim 7.

14. Adhesive composition based on amino-aldehyde resin according to claim 7, wherein urea and/or melamine is additionally used as amino compound.

15. Amino aldehyde resin prepared according to claim 6.

* * * * *